(12) United States Patent
Hatlestad et al.

(10) Patent No.: US 8,753,276 B2
(45) Date of Patent: Jun. 17, 2014

(54) PHYSIOLOGICAL RESPONSE TO POSTURE CHANGE

(75) Inventors: John D. Hatlestad, Maplewood, MN (US); Imad Libbus, St. Paul, MN (US); Aaron Lewicke, Forest Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 161 days.

(21) Appl. No.: 13/415,281

(22) Filed: Mar. 8, 2012

(65) Prior Publication Data

US 2012/0172764 A1 Jul. 5, 2012

Related U.S. Application Data

(62) Division of application No. 11/466,925, filed on Aug. 24, 2006, now Pat. No. 8,343,049.

(51) Int. Cl.
*A61B 5/00* (2006.01)
*A61B 5/02* (2006.01)
*A61B 5/08* (2006.01)
*A61B 7/00* (2006.01)
*A61N 1/362* (2006.01)

(52) U.S. Cl.
USPC ........... 600/301; 600/481; 600/485; 600/529; 600/586; 607/18

(58) Field of Classification Search
USPC ....................................................... 600/301
See application file for complete search history.

(56) References Cited

U.S. PATENT DOCUMENTS

| 4,003,379 A | 1/1977 | Ellinwood, Jr. |
| 4,308,872 A | 1/1982 | Watson et al. |
| 4,470,987 A | 9/1984 | Wurtman et al. |
| 4,576,183 A | 3/1986 | Plicchi et al. |
| 4,651,716 A | 3/1987 | Forester et al. |
| 4,884,576 A | 12/1989 | Alt |
| 4,987,897 A | 1/1991 | Funke |
| 5,025,786 A | 6/1991 | Siegel |
| 5,040,536 A | 8/1991 | Riff |
| 5,113,869 A | 5/1992 | Nappholz et al. |
| 5,117,825 A | 6/1992 | Grevious |

(Continued)

FOREIGN PATENT DOCUMENTS

| EP | 348271 | 12/1989 |
| EP | 0985374 A2 | 3/2000 |

(Continued)

OTHER PUBLICATIONS

"U.S. Appl. No. 10/267,982, Non Final Office Action mailed May 2, 2005", 7 pgs.

(Continued)

*Primary Examiner* — Patricia Mallari
*Assistant Examiner* — Michael R Bloch
(74) *Attorney, Agent, or Firm* — Schwegman, Lundberg & Woessner, P.A.

(57) ABSTRACT

In an embodiment, an implantable medical device includes a controller circuit, a posture sensing circuit, and a physiological sensing circuit. The controller circuit senses a change in a physiological signal as a result of a change in posture, and generates a response as a function of that change. In another embodiment, the controller circuit identifies a heart failure condition as a function of the change in the physiological signal.

11 Claims, 3 Drawing Sheets

(56) References Cited

U.S. PATENT DOCUMENTS

| | | |
|---|---|---|
| 5,199,428 A | 4/1993 | Obel et al. |
| 5,213,098 A | 5/1993 | Bennett et al. |
| 5,233,984 A | 8/1993 | Thompson |
| 5,233,985 A | 8/1993 | Hudrlik |
| 5,246,008 A | 9/1993 | Mueller et al. |
| 5,271,395 A | 12/1993 | Wahlstrand et al. |
| 5,282,840 A | 2/1994 | Hudrlik et al. |
| 5,284,136 A | 2/1994 | Hauck et al. |
| 5,292,343 A | 3/1994 | Blanchette et al. |
| 5,300,093 A | 4/1994 | Koestner et al. |
| 5,313,953 A | 5/1994 | Yomtov et al. |
| 5,324,309 A | 6/1994 | Kallok |
| 5,324,315 A | 6/1994 | Grevious |
| 5,342,404 A | 8/1994 | Alt et al. |
| 5,344,429 A | 9/1994 | Smits |
| 5,354,319 A | 10/1994 | Wyborny et al. |
| 5,370,665 A | 12/1994 | Hudrlik |
| 5,411,031 A | 5/1995 | Yomtov |
| 5,441,525 A | 8/1995 | Shelton et al. |
| 5,479,369 A | 12/1995 | Matsumura et al. |
| 5,501,701 A | 3/1996 | Markowitz et al. |
| 5,507,785 A | 4/1996 | Deno |
| 5,534,018 A | 7/1996 | Wahlstrand et al. |
| 5,540,728 A | 7/1996 | Shelton et al. |
| 5,593,431 A | 1/1997 | Sheldon |
| 5,626,623 A | 5/1997 | Kieval et al. |
| 5,676,686 A | 10/1997 | Jensen et al. |
| 5,706,829 A | 1/1998 | Kadri |
| 5,725,562 A | 3/1998 | Sheldon |
| 5,732,710 A | 3/1998 | Rabinovich et al. |
| 5,749,369 A | 5/1998 | Rabinovich et al. |
| 5,788,643 A | 8/1998 | Feldman |
| 5,800,464 A | 9/1998 | Kieval |
| 5,874,420 A | 2/1999 | Pelleg |
| 5,919,210 A | 7/1999 | Lurie et al. |
| 5,957,957 A | 9/1999 | Sheldon |
| 6,002,963 A | 12/1999 | Mouchawar et al. |
| 6,015,388 A | 1/2000 | Sackner et al. |
| 6,044,297 A | 3/2000 | Sheldon et al. |
| 6,047,203 A | 4/2000 | Sackner et al. |
| 6,049,730 A | 4/2000 | Kristbjarnarson |
| 6,049,735 A | 4/2000 | Hartley et al. |
| 6,076,015 A | 6/2000 | Hartley et al. |
| 6,078,834 A | 6/2000 | Lurie et al. |
| 6,104,949 A | 8/2000 | Pitts et al. |
| 6,317,631 B1 | 11/2001 | Ben-Haim et al. |
| 6,351,672 B1 * | 2/2002 | Park et al. .................. 607/19 |
| 6,473,640 B1 | 10/2002 | Erlebacher |
| 6,512,949 B1 | 1/2003 | Combs et al. |
| 6,616,607 B2 | 9/2003 | Hashimoto et al. |
| 6,625,492 B2 | 9/2003 | Florio et al. |
| 6,647,295 B2 | 11/2003 | Florio et al. |
| 6,719,701 B2 | 4/2004 | Lade |
| 6,733,464 B2 | 5/2004 | Olbrich et al. |
| 6,738,666 B1 | 5/2004 | Park et al. |
| 6,748,271 B2 | 6/2004 | Spinelli et al. |
| 6,752,765 B1 | 6/2004 | Jensen et al. |
| 6,829,507 B1 | 12/2004 | Lidman et al. |
| 6,912,420 B2 | 6/2005 | Scheiner et al. |
| 6,937,900 B1 | 8/2005 | Pianca et al. |
| 6,949,075 B2 | 9/2005 | Hatlesad et al. |
| 7,177,681 B2 | 2/2007 | Zhu et al. |
| 7,191,000 B2 | 3/2007 | Zhu et al. |
| 7,226,422 B2 | 6/2007 | Hatlestsad et al. |
| 7,333,854 B1 | 2/2008 | Brewer et al. |
| 7,384,395 B2 | 6/2008 | Hatlestsad et al. |
| 7,422,560 B2 | 9/2008 | Hatlestsad et al. |
| 7,424,321 B2 | 9/2008 | Wariar et al. |
| 7,480,528 B2 | 1/2009 | Brockway et al. |
| 7,662,101 B2 | 2/2010 | Lee et al. |
| 7,819,804 B2 | 10/2010 | Hatlestad et al. |
| 8,065,010 B2 | 11/2011 | Brockway et al. |
| 8,343,049 B2 | 1/2013 | Hatlestad et al. |
| 2002/0004670 A1 | 1/2002 | Florio et al. |
| 2002/0032386 A1 | 3/2002 | Sackner et al. |
| 2002/0147475 A1 | 10/2002 | Scheiner et al. |
| 2002/0170193 A1 | 11/2002 | Townsend et al. |
| 2003/0045910 A1 * | 3/2003 | Sorensen et al. ................ 607/23 |
| 2003/0055461 A1 | 3/2003 | Girouard et al. |
| 2003/0144595 A1 | 7/2003 | Lade |
| 2004/0073128 A1 | 4/2004 | Hatlestad et al. |
| 2004/0106962 A1 | 6/2004 | Mai et al. |
| 2004/0172080 A1 | 9/2004 | Stadler et al. |
| 2004/0215263 A1 | 10/2004 | Virag et al. |
| 2004/0215265 A1 | 10/2004 | Keizer |
| 2005/0021098 A1 | 1/2005 | Spinelli et al. |
| 2005/0038327 A1 | 2/2005 | Tanaka et al. |
| 2005/0145246 A1 | 7/2005 | Hartley et al. |
| 2005/0283197 A1 | 12/2005 | Daum et al. |
| 2006/0020295 A1 | 1/2006 | Brockway et al. |
| 2006/0025699 A1 | 2/2006 | Maile et al. |
| 2006/0094967 A1 | 5/2006 | Bennett et al. |
| 2006/0241513 A1 | 10/2006 | Hatlestad et al. |
| 2007/0106130 A1 | 5/2007 | Hatlestsad et al. |
| 2007/0118054 A1 | 5/2007 | Pinhas et al. |
| 2007/0129643 A1 | 6/2007 | Kwok et al. |
| 2007/0156057 A1 | 7/2007 | Cho et al. |
| 2008/0045852 A1 | 2/2008 | Hatlestsad et al. |
| 2008/0082001 A1 | 4/2008 | Hatlestad et al. |
| 2009/0005697 A1 | 1/2009 | Hatlestsad et al. |
| 2011/0009709 A1 | 1/2011 | Hatlestsad et al. |

FOREIGN PATENT DOCUMENTS

| | | |
|---|---|---|
| EP | 0985429 A2 | 3/2000 |
| EP | 1151719 A2 | 11/2001 |
| EP | 1238630 A2 | 9/2002 |
| EP | 1115350 B1 | 8/2003 |
| EP | 1011803 B1 | 9/2004 |
| EP | 0985374 B1 | 12/2004 |
| EP | 0985429 B1 | 12/2004 |
| EP | 2394575 A1 | 12/2011 |
| JP | 03109277 U | 11/1991 |
| JP | 4-082538 | 3/1992 |
| JP | 05048904 A2 | 2/1993 |
| JP | 05048904 | 6/1993 |
| JP | 06-327653 A | 11/1994 |
| JP | 2003-088512 | 3/2003 |
| JP | 2003-088512 A | 3/2003 |
| JP | 2004081854 | 3/2004 |
| JP | 2006327653 A2 | 12/2006 |
| JP | 06-327653 | 11/2009 |
| WO | WO-8400227 | 1/1984 |
| WO | WO-9800197 A1 | 1/1998 |
| WO | WO-9833554 A1 | 8/1998 |
| WO | WO-0018317 A2 | 4/2000 |
| WO | WO-0119426 A2 | 3/2001 |
| WO | WO-0178577 A2 | 10/2001 |
| WO | WO-0240096 A1 | 5/2002 |
| WO | WO-2004012815 A1 | 2/2004 |
| WO | WO-2004047638 A1 | 6/2004 |
| WO | WO-2004050178 A1 | 6/2004 |
| WO | WO-2004060166 A2 | 7/2004 |
| WO | WO-2004095306 A1 | 11/2004 |
| WO | WO-2005046472 A1 | 5/2005 |
| WO | WO-2005046472 A2 | 5/2005 |
| WO | WO-2005074361 A2 | 8/2005 |

OTHER PUBLICATIONS

"U.S. Appl. No. 10/267,982, Notice of Allowance mailed Jun. 2, 2006", 7 pgs.

"U.S. Appl. No. 10/267,982, Notice of Allowance mailed Oct. 3, 2006", 7 pgs.

"U.S. Appl. No. 10/267,982, Notice of Allowance mailed Dec. 29, 2005", 6 pgs.

"U.S. Appl. No. 10/267,982, Response filed Oct. 3, 2005 to Non-Final Office Action mailed May 2, 2005", 15 pgs.

"U.S. Appl. No. 10/267,982, Supplemental Amendment filed Jan. 18, 2006", 12 pgs.

"U.S. Appl. No. 10/267,982, Supplemental Amendment filed Aug. 29, 2006", 13 pgs.

(56) References Cited

OTHER PUBLICATIONS

"U.S. Appl. No. 11/466,925, Final Office Action mailed Aug. 11, 2011", 10 pgs.
"U.S. Appl. No. 11/466,925, Non-Final Office Action mailed Feb. 18, 2011", 11 pgs.
"U.S. Appl. No. 11/466,925, Notice of Allowance mailed Oct. 31, 2011", 8 pgs.
"U.S. Appl. No. 11/466,925, Response filed May 16, 2011 to Non-Final Office Action mailed Feb. 18, 2011", 10 pgs.
"U.S. Appl. No. 11/466,925, Response filed Oct. 10, 2011 to Final Office Action mailed Aug. 11, 2011", 14 pgs.
"U.S. Appl. No. 11/466,925, Response filed Oct. 19, 2010 to Restriction Requirement mailed Sep. 23, 2010", 10 pgs.
"U.S. Appl. No. 11/466,925, Restriction Requirement mailed Sep. 23, 2010", 9 pgs.
"U.S. Appl. No. 11/619,821, Notice of Allowance Mailed Aug. 24, 2007", 7 pgs.
"U.S. Appl. No. 11/619,821, Response and Preliminary Amendment filed Jul. 16, 2007 to Restriction Requirement mailed Jun. 14, 2007", 8 pgs.
"U.S. Appl. No. 11/619,821, Restriction Requirement mailed Jun. 14, 2007", 5 pgs.
"U.S. Appl. No. 11/926,425, Amendment filed Jul. 1, 2008 in Response to Notice of Allowance mailed Apr. 1, 2008", 4 pgs.
"U.S. Appl. No. 11/926,425, Notice of Allowance mailed Apr. 1, 2008", 6 pgs.
"U.S. Appl. No. 11/926,425, Preliminary Amendment mailed Nov. 21, 2007", 7 pgs.
"U.S. Appl. No. 11/926,425, Response to Rule 312 Communication mailed Aug. 8, 2008", 2 pgs.
"U.S. Appl. No. 12/204,152, Non-Final Office Action mailed Mar. 19, 2010", 5 pgs.
"U.S. Appl. No. 12/204,152, Notice of Allowance mailed Jun. 23, 2010", 4 Pgs.
"U.S. Appl. No. 12/204,152, Response filed May 24, 2010 to Non Final Office Action mailed Mar. 19, 2010", 7 pgs.
"European Application Serial No. 03786528.4, Communication mailed Aug. 17, 2009", 4 pgs.
"European Application Serial No. 03786528.4, Communication Pursuant to Art. 94(3) EPC mailed Nov. 15, 2011", 6 pgs.
"European Application Serial No. 03786528.4, Response filed Jan. 29, 2010 to Communication mailed Aug. 17, 2009", 19 pgs.
"European Application Serial No. 11177688.6, European Search Report mailed Nov. 15, 2011", 5 pgs.
"International Application Serial No. PCT/US2003/032553, International Search Report mailed Jun. 17, 2004", 4 pgs.
"Japanese Application Serial No. 2005-510603, Amendment filed Mar. 30, 2010 in Response to Office Action mailed Dec. 2, 2009", (w/ English Translation of Amended Claims), 37 pgs.
"Japanese Application Serial No. 2005-510603, Notice of Allowance mailed Apr. 20, 2010", 3 pgs.
"Japanese Application Serial No. 2005-510603, Office Action mailed Dec. 2, 2009", (w/ English Translation), 6 pgs.
Handa, T, "Orthopnea and Respiratory Distress", Clinician, 22(10), (Oct. 10, 1996), 2243-2246.
Hatlestad, John D, et al., "Detection of Congestion From Monitoring Patient Response to a Recumbent Position", U.S. Appl. No. 11/619,821, filed Jan. 4, 2007, 27 pgs.
Kubo, S. H., "Circulatory autoregulation in chronic congestive heart failure: responses to head-up tilt in 41 patients.", Am J Cardiol., 52(5), (Sep. 1, 1983), 512-8.
Larsen, F., et al., "Influence of furosemide and body posture on transthoracic electrical impedance in AMI", Chest, 90(5), (733-7), Nov. 1986.
Levine, T. B., et al., "The Neurohumoral and Hemodynamic Response to Orthostatic Tilt in Patients with Congestive Heart Failure.", Circulation, 67(5), (May 1983), 1070-1075.
Miyamoto, S., "Effects of Posture on Cardiac Autonomic Nervous Activity in Patients with Congestive Heart Failure", Journal of the American College of Cardiology, 37(7), (Jun. 1, 2001), 1788-1793.

Sanderson, John E, et al., "Impact of changes in respiratory frequency and posture on power spectral analysis of heart rate and systolic blood pressure variability in normal subjects and patients with heart failure", Clinical Science, vol. 91, (1996), 35-43.
U.S. Appl. No. 09/919,483, Non Final Office Action mailed Aug. 22, 2002, 5 pgs.
U.S. Appl. No. 09/919,483, Non Final Office Action mailed Sep. 22, 2003, 6 pgs.
U.S. Appl. No. 09/919,483, Non Final Office Action mailed Oct. 4, 2004, 8 pgs.
U.S. Appl. No. 09/919,483, Notice of Allowance mailed Feb. 6, 2003, 6 pgs.
U.S. Appl. No. 09/919,483, Notice of Allowance mailed Feb. 24, 2006, 7 pgs.
U.S. Appl. No. 09/919,483, Notice of Allowance mailed Mar. 22, 2005, 6 pgs.
U.S. Appl. No. 09/919,483, Notice of Allowance mailed Sep. 21, 2006, 5 pgs.
U.S. Appl. No. 09/919,483, Response filed Nov. 22, 2002 to Non Final Office Action mailed Aug. 22, 2002, 8 pgs.
U.S. Appl. No. 09/919,483, Response filed Dec. 22, 2003 to Non Final Office Action mailed Sep. 22, 2003, 12 pgs.
U.S. Appl. No. 09/919,483, Response filed Dec. 30, 2004 to Non Final Office Action mailed Oct. 4, 2004, 13 pgs.
U.S. Appl. No. 09/919,483, Supplemental Notice of Allowability mailed Apr. 14, 2006, 2 pgs.
U.S. Appl. No. 10/267,982, Response filed Oct. 3, 2005 to Non-Final Office Action mailed May 2, 2005, 15 pgs.
U.S. Appl. No. 10/411,795, Non Final Office Action mailed Apr. 14, 2006, 13 pgs.
U.S. Appl. No. 10/411,795, Non Final Office Action mailed Nov. 1, 2005, 12 pgs.
U.S. Appl. No. 10/411,795, Notice of Allowance mailed Sep. 29, 2006, 5 pgs.
U.S. Appl. No. 10/411,795, Response filed Jan. 13, 2006 to Non Final Office Action mailed Nov. 1, 2005, 22 pgs.
U.S. Appl. No. 10/411,795, Response filed Jul. 11, 2006 to Non Final Office Action mailed Apr. 14, 2006, 22 pgs.
U.S. Appl. No. 10/897,856, Advisory Action mailed Jun. 17, 2008, 3 pgs.
U.S. Appl. No. 10/897,856, Final Office Action mailed Jan. 4, 2008, 15 pgs.
U.S. Appl. No. 10/897,856, Non Final Office Action mailed Oct. 4, 2006, 15 pgs.
U.S. Appl. No. 10/897,856, Notice of Allowance mailed Sep. 15, 2008, 6 pgs.
U.S. Appl. No. 10/897,856, Response filed Jan. 2, 2007 to Non Final Office Action mailed Oct. 4, 2006, 24 pgs.
U.S. Appl. No. 10/897,856, Response filed Mar. 4, 2008 to Final Office Action mailed Jan. 4, 2008, 24 pgs.
U.S. Appl. No. 10/897,856, Supplemental Notice of Allowability mailed Oct. 22, 2008, 3 pgs.
U.S. Appl. No. 10/897,856, Supplemental Notice of Allowability mailed Dec. 3, 2008, 3 pgs.
U.S. Appl. No. 11/291,479, Final Office Action mailed Feb. 2, 2010, 9 pgs.
U.S. Appl. No. 11/291,479, Final Office Action mailed Nov. 13, 2008, 8 pgs.
U.S. Appl. No. 11/291,479, Non-Final Office Action mailed Feb. 19, 2008, 8 pgs.
U.S. Appl. No. 11/291,479, Non-Final Office Action mailed May 26, 2009, 8 pgs.
U.S. Appl. No. 11/291,479, Non-Final Office Action Mailed Jul. 25, 2007, 10 pgs.
U.S. Appl. No. 11/291,479, Response filed Jul. 21, 2008 to Non-Final Office Action mailed Feb. 19, 2008, 8 pgs.
U.S. Appl. No. 11/291,479, Response filed Oct. 26, 2009 to Non Final Office Action mailed May 26, 2009, 10 pgs.
U.S. Appl. No. 11/291,479, Response filed Nov. 21, 2007 to Non-Final Office Action mailed Jul. 25, 2007, 8 pgs.
U.S. Appl. No. 11/291,479, Response filed Mar. 4, 2009 to Final Office Action mailed Nov. 13, 2008, 10 pgs.

(56) References Cited

OTHER PUBLICATIONS

U.S. Appl. No. 11/466,925, Notice of Allowance mailed Sep. 4, 2012, 5 pgs.
U.S. Appl. No. 12/319,642, Non Final Office Action mailed Dec. 21, 2010, 8 pgs.
U.S. Appl. No. 12/319,642, Notice of Allowance mailed Apr. 13, 2011, 5 pgs.
U.S. Appl. No. 12/319,642, Notice of Allowance mailed Jul. 19, 2011, 5 pgs.
U.S. Appl. No. 12/319,642, Response filed Mar. 21, 2011 to Non Final Office Action mailed Dec. 21, 2010, 14 pgs.
U.S. Appl. No. 12/887,680, Response filed Oct. 24, 2013 to Restriction Requirement mailed Sep. 24, 2013, 7 pgs.
U.S. Appl. No. 12/887,680, Restriction Requirement mailed Sep. 24, 2013, 5 pgs.
European Application Serial No. 03786528.4, Response filed Mar. 23, 2012 to Office Action mailed Nov. 15, 2011, 14 pgs.
European Application Serial No. 05806944.4, Office Action mailed Apr. 14, 2008, 8 pgs.
European Application Serial No. 05806944.4, Response filed Oct. 17, 2008 to Office Action mailed Apr. 14, 2008, 22 pgs.
European Application Serial No. 10173334.3, Examination Notification Art. 94(3) mailed Aug. 24, 2011, 4 pgs.
European Application Serial No. 10173334.3, Extended European Search Report mailed Oct. 15, 2010, 10 pgs.
European Application Serial No. 10173334.3, Response filed May 23, 2011 to Office Action mailed Nov. 29, 2010, 8 pgs.
International Application Serial No. PCT/US2005/025235, International Search Report and Written Opinion mailed Apr. 4, 2006, 20 pgs.
International Application Serial No. PCT/US2005/025235, Invitation to Pay Additional Fees and Partial Search Report mailed Jan. 27, 2006, 9 pgs.
Japanese Application Serial No. 2007-522593, Response filed Jun. 1, 2011 to Non Final Office Action mailed Dec. 27, 2010, (w/ English Translation of Amended Claims), 31 pgs.
Japanese Application Serial No. 2007-533593, Office Action mailed Dec. 27, 2010, (w/ English Translation), 4 pgs.
"Medtronic Announces European Release of Innovative InSync Sentry tm Cardiac Resynchronization Therapy Defibrillator", [online]. [retrieved Nov. 23, 2005]. Retrieved from the Internet: <URL: http://www.medtronic.com/newsroom/news_20040614a.html>, (2004), 2 pgs.
"Medtronic: Insync Sentry 7298", www.medtronic.com, Reference Manual, (2004), 420 pgs.
Aaron, S. D, et al., "How accurate is spirometry at predicting restrictive pulmonary impairment?", Chest, 115(3), XP002362629 ISSN: 0012-3692, (Mar. 1999), 869-873.
Aaron, S. D, et al., "How accurate is spirometry at predicting restrictive pulmonary impairment?", Chest, 115(3), (Mar. 1999), 869-73.
Berman, Irwin R, et al., "Transthoracic electrical impedance s a guide to intravascular overload", Archives of Surgery, 102(1), (Jan. 1971), 61-64.
Charach, Gideon, et al., "Transthoracic monitoring of the impedance of the right lung in patients with cardiogenic pulmonary edema", Critical Care Medicine, 29(6), (Jun. 2001), 1137-44.
Cooke, W. H., et al., "Human responses to upright tilt: a window on central autonomic integration", J Physiol., 517( Pt 2), (Jun. 1, 1999), 617-28.
Daum, Douglas R, "Systems and Methods for Hypotension", U.S. Appl. No. 11/141,260, filed May 31, 2005, 51 pgs.

Ellenbogen, Kenneth A, et al., "Rate-adaptive pacing based on impedance-derived minute ventilation", Clinical Cardiac Pacing, Philadelphia : Saunders, (1995), 219-233.
Hatlestad, J. D, et al., "Physiological Response to Posture Change", U.S. Appl. No. 11/466,925, filed Aug. 24, 2006, 21 pgs.
Kadhiresan, Veerichetty, et al., "Cardiopulmonary Functional Status Assessment Via Heart Rate Response Dectection by Implantable Cardiac Device", U.S. Appl. No. 10/914,632, filed Aug. 9, 2004, 18 pgs.
Kusumoto, Fred M, et al., "Medical Progress: Cardiac Pacing", New England Journal of Medicine, 334(2), (Jan. 11, 1996), 89-98.
Lau, C P, et al., "Rate-responsive pacing with a pacemaker that detects respiratory rate (Biorate): clinical advantages and complications", Clinical Cardiology, 11(5), (May 1988), 318-24.
Lucas, C., "Congestive Heart Failure, Freedom from Congestion Predicts Good Survival Despite Previous Class IV Symptoms of Heart Failure", American Heart Journal, 140(6), (Dec. 2000), 840-847.
Luepker, R. V., et al., "Transthoracic Electrical Impedance: Quantitative Evaluation of a Non-Invasive Measure of Thoracic Fluid Volume", American Heart Journal, 85(1), (Jan. 1973), 83-93.
Mai, J., et al., "Enhanced Rate Response Algorithm for Orthostatic Compensation Pacing", Pacing Clin Electrophysiol, 23, Naspe Abstracts, Abstract No. 678, (Apr. 2000), 722.
Michal, Eugene T., et al., "Methods and Compositions to Treat Myocardiac Conditions", U.S. Appl. No. 10/802,955, filed Mar. 16, 2004, 113 pgs.
Pomerantz, M, et al., "Transthoracic electrical impedance for the early detection of pulmonary edema", Surgery, 66(1), (Jul. 1969), 260-8.
Radisic, M, et al., "Functional assembly of engineered myocardium by electrical stimulation of cardiac myocytes cultured on scaffolds", Proc Natl Acad Sci U S A., 101(52), (Dec. 28, 2004), 18129-18134.
Rosborough, John P, et al., "Electrical Therapy for Pulseless Electrical Activity", NASPE, 23(4), Part II, Abstract, (Apr. 2000), 591.
Shoemaker, William C, et al., "Multicenter trial of a new thoracic electrical bioimpedance device for cardiac output estimation", Critical Care Medicine, 22(12), (Dec. 1994), 1907-1912.
Spinelli, J. C., "Method and System for Treatment of Neurocardiogenic Syncope", U.S. Appl. No. 10/862,831, filed Jun. 7, 2004, 15 pgs.
Stahmann, Jeffrey E, et al., "Detection of Pleural Effusion Using Transthoracic Impedance", U.S. Appl. No. 11/132,109, filed May 18, 2005, 47 pgs.
Stevenson, L. W., et al., "The limited reliability of physical signs for estimating hemodynamics in chronic heart failure", JAMA., 261(6), (Feb. 19, 1989), 884-8.
Viirola, H, et al., "Controlled growth of antimony-doped tin dioxide thin films by atomic layer epitaxy", Thin Solid Films, 251, (Nov. 1994), 127-135.
Viirola, H, et al., "Controlled growth of tin dioxide thin films by atomic layer epitaxy", Thin Solid Films, 249(2), (Sep. 1994), 144-149.
Visokay, M R, "Application of HfSiON as a gate dielectric material", Applied Physics Letters, 80(17), (Apr. 2002), 3183-3185.
Wuerz, Richard C, et al., "Effects of prehospital medications on mortality and length of stay in congestive heart failure", Annals of Emergency Medicine, 21(6), (Jun. 1992), 669-74.
Zhu, Q., et al., "Cardiac Rhythm Management System for Edema", U.S. Appl. No. 11/673,699, filed Jan. 12, 2007, 22 pgs.

* cited by examiner

PHYSIOLOGICAL RESPONSE TO POSTURE CHANGE

CROSS-REFERENCE TO RELATED APPLICATIONS

This patent application is a divisional of U.S. patent application Ser. No. 11/466,925, filed Aug. 24, 2006, which is incorporated herein by reference in its entirety.

TECHNICAL FIELD

Various embodiments relate to the field of implantable medical devices, and in an embodiment, but not by way of limitation, to the detection by an implantable medical device of a physiological response to posture changes.

BACKGROUND

A person's health status may be determined by analyzing physiological parameters such as heart rate, respiration pattern, and blood pressure, just to list a few. These physiological parameters may follow different patterns for a healthy individual versus a person who is suffering from some form of ill health. Some physiological parameters are affected by the posture of the body. Additionally, the present inventors have recognized that the response of these parameters to changes in posture may be affected by the person's state of health. Consequently, the present inventors have recognized that medical and health care profession would benefit from a system and method to detect, capture, and analyze the effect of posture change on such physiological parameters.

SUMMARY

In certain examples, an implantable medical device includes a controller circuit, a posture sensing circuit, and a physiological sensing circuit. The controller circuit senses a change in a physiological signal as a result of a change in posture, and can optionally respond to that change. In certain examples, the controller circuit identifies a heart failure condition or status using the change in the physiological signal.

This summary is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe similar components throughout the several views. The drawings illustrate generally, by way of example, but not by way of limitation, various examples discussed in the present document.

DETAILED DESCRIPTION

The following detailed description refers to the accompanying drawings which form a part hereof, and in which is shown by way of illustration specific embodiments in which the invention may be practiced. These embodiments, which are sometimes referred to as examples, are discussed in sufficient detail to enable those skilled in the art to practice the invention, and such embodiments may be combined, or that other embodiments may be utilized and that structural, logical and electrical changes may be made without departing from the scope of the present invention. The following detailed description provides examples, and the scope of the present invention is defined by the appended claims and their equivalents.

It should be noted that references to "an", "one", or "various" embodiments in this disclosure are not necessarily to the same embodiment, and such references contemplate more than one embodiment.

The system and method described herein provide a system and method to detect a physiological response to a posture change. In one or more examples, the physiological responses include one or more of a change in heart rate, a change in heart rate variability, a change in heart sounds, a change in respiration rate, and a change in blood pressure. The change in posture may include one or more of a change from a more upright posture to a more recumbent posture, a change from a more recumbent posture to a more upright posture, and a change within a recumbent posture (e.g., changing from a supine position to a right lateral decubitus position). The upright posture may include a standing posture or sitting posture or both, and the recumbent posture may include one or more of supine, prone, right lateral decubitus, and left lateral decubitus postures.

Figure 1:
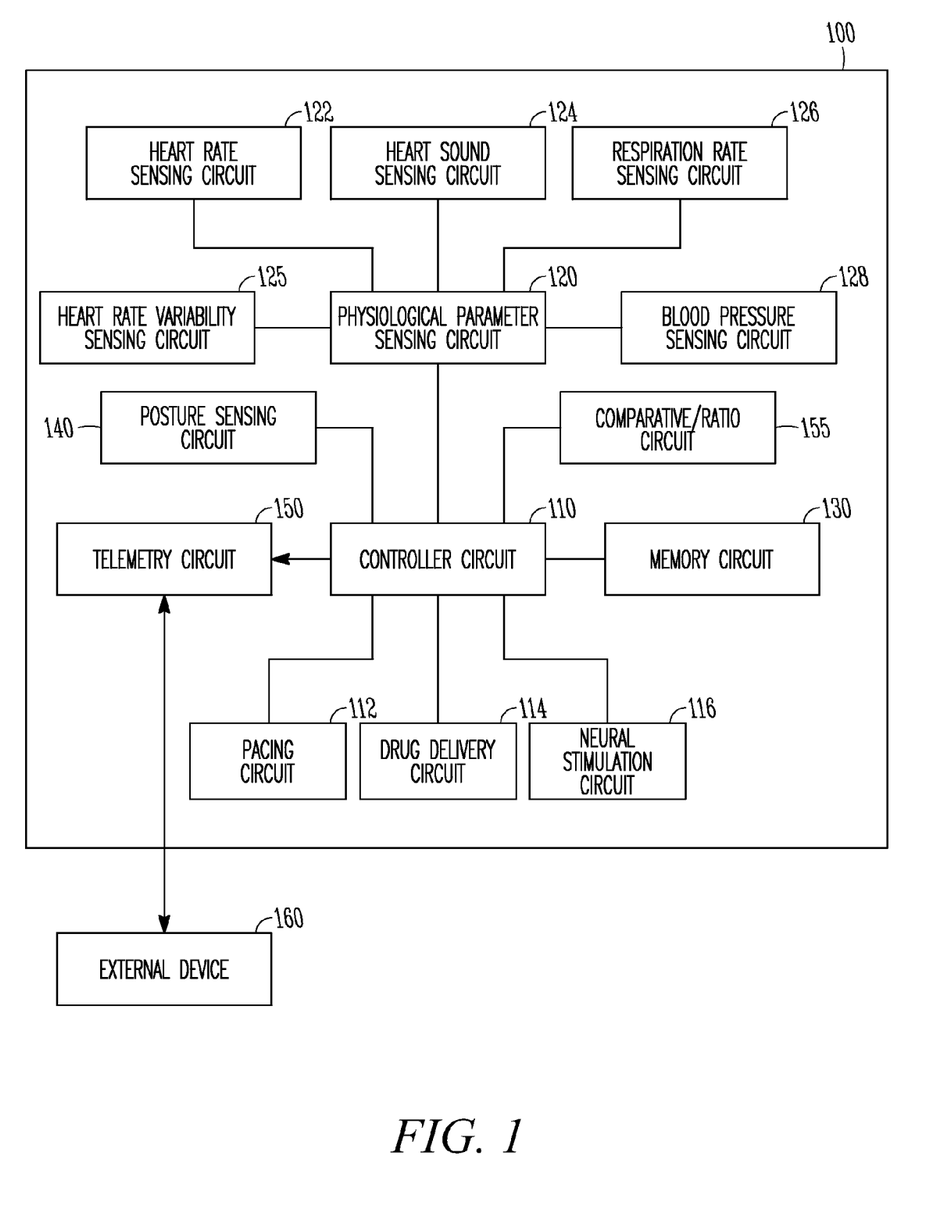
FIG. 1 illustrates a block diagram of an example embodiment of an implantable medical device.

FIG. 1 illustrates an example of an implantable medical device 100. In this example, the device 100 includes a controller circuit 110. The device 100 further includes a posture sensing circuit 140. The posture sensing circuit 140 may include one or more of a tilt switch, a single axis accelerometer, and a multi-axis accelerometer. The device 100 can include one or more of a memory circuit 130, an energy delivery circuit 112 to deliver energy to a heart, a drug delivery circuit 114, a neural stimulation circuit 116, a physiological parameter sensing circuit 120, a telemetry circuit 150, a comparator circuit 155, and an activity sensing circuit 118—any or all of which can be coupled to the controller circuit 110. The telemetry circuit 150 is generally capable of being wirelessly coupled to an external device 160. The physiological parameter sensing circuit 120 can include one or more of several sub-circuits, such as a heart rate sensing circuit 122, a heart sound sensing circuit 124, a heart rate variability sensing circuit 125, a respiration sensing circuit 126, or a blood pressure sensing circuit 128. The energy delivery circuit 112 may include one or more of a pacing circuit, an anti-tachyarrhythmia pacing (ATP) circuit, a cardiac resynchronization therapy (CRT) circuit, or a defibrillation or cardioversion circuit.

In an example, the device 100 is implanted into a patient. The posture sensing circuit 140 senses the patient's posture, and transmits a resulting posture signal to the controller circuit 110. For example, this posture signal may indicate that the patient is recumbent, seated, standing, prone, supine, and/or in a right or left lateral decubitus position. Substantially concurrently, the physiological signal sensing circuit 120 senses at least one other physiological signal—different from posture, but which may be affected by posture. Examples of such physiological signals may include heart rate, heart sound, heart rate variability, respiration, blood pressure, or the like. The physiological sensing circuit 120 transmits to the controller circuit 110 a physiological signal indicative of the sensed physiological parameter. In response to the received posture and physiological signals, the controller circuit 110 determines whether there is a change in the physiological signal in response to a change in the patient's posture. The controller circuit 110 can further generate a response as a function of the posture and physiological signals, such as in response to a change in the physiological signal resulting from a change in the patient's posture. Such a response can include transmitting a control, alert, or other signal to one or more of the energy delivery circuit 112, the drug delivery circuit 114, the neural stimulation circuit 116, and the telemetry circuit 150. In certain examples, such a response can indicate whether a patient's heart failure condition is improving or getting worse.

In certain examples, the physiological signal is a heart rate, and the controller 110 determines a change in heart rate caused by a change in posture. A normal patient's heart rate typically increases upon standing up. However, while a patient with heart failure will also experience an increase in heart rate upon standing up, such increase is believed to generally be less than the corresponding increase for the normal patient. Thus, in certain examples, the controller 110 can compare the heart rate response to posture to a normal patient's response to determine an indication of whether the patient has heart failure, or whether the patient's heart failure is improving or worsening. The heart failure patient's smaller increase in heart rate upon standing can be used in several different ways. For example, the device may use this information to identify that a patient is experiencing heart failure, to identify whether the heart failure is improving or worsening, or both. For example, if a heart failure patient's heart rate response to a change in posture, such as standing, trends towards a normal subject's response, then the heart failure patient's condition can be deemed to be improving. If the heart failure patient's heart rate response to the posture change trends away from a normal person's response (e.g., the patient's trend is toward an even smaller increase in heart rate upon standing), the heart failure patient's condition can be deemed to be getting worse. In certain examples, in response to the improving, worsening, or constancy of the patient's heart failure condition, the controller circuit 110 can transmit a signal to the energy delivery circuit 112, drug delivery circuit 114, neural stimulation circuit 116, or telemetry circuit 150, such as to initiate or adjust a responsive heart failure or other therapy or to deliver an alert to the patient or a caregiver.

In another example, the blood pressure sensing circuit 128 senses a change in a person's blood pressure resulting from a change in posture. Changes in a normal patient's blood pressure are typically quite small when going from a more recumbent position to a more upright position due to a compensatory baro-reflex response of the body to maintain blood pressure homeostasis. However, a person suffering from heart failure typically experiences a greater decrease in blood pressure than a normal person. Information about the degree of change in blood pressure in response to a posture change (or a comparison of this response to the response of a normal patient) can be used by the controller circuit 110 to determine whether heart failure is present, improving, or worsening. As discussed above, the controller circuit 110 can use this information to identify heart failure or its improvement or worsening, and can optionally transmit a responsive signal to one or more of the energy delivery circuit 112, the drug delivery circuit 114, or the neural stimulation circuit 116, such as to initiate or adjust a responsive therapy, or to the telemetry circuit 150, such as to deliver an alert to the patient or a caregiver.

In another example, the heart sound sensing circuit 124 senses a change in one or more heart sounds caused by a change in the patient's posture. The sensed heart sounds may be the normal heart sounds S1 and S2 caused by the closure of the mitral and tricuspid valves, and the closure of the aortic and pulmonary valves respectively. The sensed heart sounds may also include the abnormal heart sounds S3, S4, and mitral regurgitation. The S3 and S4 heart sounds both relate to ventricular diastolic filling. A normal patient will typically experience an increase in heart rate upon becoming more upright. This also typically results in an increase in heart sound energy. However, a heart failure patient will typically experience a smaller increase in heart rate upon changing to a more upright posture. As a result, the heart failure patient will typically experience a smaller increase in heart sound energy than a normal person. This information (or a comparison of this response to the response of a normal patient) can be used to determine whether heart failure is present, improving, or worsening, or if therapy should be initiated or adjusted in response to the change, or if a responsive alert should be delivered to the patient or a caregiver. While this example indicates that heart sound energy will not increase in a heart failure patient as much as in a normal patient, other effects relating to heart sounds for other types of heart failure conditions or other diseases may manifest themselves.

In another example, the heart rate variability (HRV) sensing circuit 125 senses a change in heart rate variability in response to a change in posture. A normal person's heart rate varies in response to several factors, including a change in posture. However, it is believed that a heart failure patient's heart rate variability will exhibit a smaller change in response to a posture change than a normal person. This information (or a comparison of this response to the response of a normal patient) can be used to determine whether heart failure is present, improving, or worsening, or if therapy should be initiated or adjusted in response to the change, or if a responsive alert should be delivered to the patient or a caregiver. In certain examples, frequency components of HRV may be extracted such as a high frequency (HF) component of HRV and a low frequency (LF) component of HRV. An LF/HF ratio can be used to assess sympathetic/parasympathetic balance of the autonomic nervous system. For a healthy individual, the LF/HF ratio may change by as much as 20% when transitioning a supine to an upright posture. However, it is believed that a heart failure patient will not experience as much of a change in LF/HF ratio in response to such a postural transition since sympathetic levels are already elevated. Similarly, this information (or a comparison of this response to the response of a normal patient) can be used to determine whether heart failure is present, improving, or worsening, or if therapy should be initiated or adjusted in response to the change, or if a responsive alert should be delivered to the patient or a caregiver.

In another example, the respiration rate sensing circuit 126 senses a change in respiration rate in response to a change in posture. A normal person will typically experience an increase in respiration rate upon becoming more upright. By contrast, it is believed that a heart failure patient will typically experience a decrease in respiration rate upon becoming more upright. This results from thoracic fluid accumulation in a recumbent heart failure patient that can make breathing difficult when recumbent, resulting in a compensatory increase in respiration rate when recumbent. Upon becoming more upright, some thoracic fluid moves out of or away from the lungs, thereby making it easier to breathe. This information (or a comparison of this response to the response of a normal patient) can be used to determine whether heart failure is present, improving, or worsening, or if therapy should be initiated or adjusted in response to the change, or if a responsive alert should be delivered to the patient or a caregiver.

As discussed above, the controller circuit 110 may be coupled to one or more of an energy delivery circuit 112, a drug delivery circuit 114, or a neural stimulation circuit 116. When coupled to the energy delivery circuit 112, any pacing or cardiac resynchronization therapy delivered to the patient may be based at least in part on the information received from the posture sensing circuit 140 and the physiological parameter sensing circuit 120. The pacing or cardiac resynchronization therapy can be adjusted many different ways, such as by changing the rate of the delivered pulses, changing the amplitude of the delivered pulses, changing the pulsewidth of the delivered pulses, adjusting the location in the patient's heart where the pacing pulses are delivered, adjusting AV-delay, inter-ventricular delay, intra-ventricular delay, or adjusting anti-tachyarrhythmia therapy.

In certain examples, the controller circuit 110 is coupled to a neural stimulation circuit 116. The controller circuit 110 can cause the neural stimulation circuit 116 to transmit one or more stimulation pulses to the autonomic nervous system (ANS) in response to a postural change in one or more physiological signals, where such stimulation of the ANS is different from issuing a stimulation pulse to capture cardiac tissue to evoke a resulting heart contraction. For example, if the heart rate variability sensing circuit 125 senses a lesser change HRV when the patient changes posture, then one or more responsive neurostimulation pulses delivered to one or more ANS locations to influence the autonomic balance and obtain a more normal HRV response to posture.

In certain examples, the device 100 can include a drug delivery circuit 114 coupled to or included in the controller circuit 110. Using the physiological response to posture information discussed above, a pharmaceutical or other substance may be titrated into the patient. For example, if over time the patient exhibits a smaller heart rate increase upon becoming more upright, a diuretic or one or more pharmaceuticals may be delivered to patient that relieve pulmonary fluid congestion. In certain examples, a cardiac resynchronization therapy may be additionally initiated or adjusted by the energy delivery circuit 112, such as to attempt to increase or restore the heart rate increase upon becoming upright.

In certain examples, the device 100 determines the extent of the postural change in the physiological signal by computing one or more ratios. In other examples, the extent of the postural change may be determined by a difference or other mathematical relationship. In certain examples, the computation of the ration or other mathematical relationship may use a comparator circuit 155 that is coupled to or incorporated in the controller circuit 110. For example, this can include calculating a ratio of a physiological signal in a first posture to the physiological signal in a second posture. This ratio can be computed for a healthy person and stored in the memory circuit 130 or the external device 160. The device 100 calculates a similar ratio for the particular patient in which the device is implanted, such as by using information received from the physiological sensing circuit 120 and the posture sensing circuit 140. These ratios can then be compared at a particular time or over a time period, such as to determine the particular patient's health status, which may include information about improvement or worsening of such health status, particularly with respect to heart failure. In certain examples, the ratio is calculated as:

$$100*(RPP1/RPP2-1)$$

In the above equation, RPP1 relates to a resting physiological parameter value while in a first posture, and RPP2 relates to a resting physiological parameter while in a second posture. The activity sensing circuit 118 may be used to determine periods when the person is at rest. Examples of physiological parameters that can be used in the above ratio include, by way of example, but not by way of limitation, heart rate, heart rate variability, heart sound amplitude, respiration, blood pressure, or other physiological parameter that is affected by posture. Additionally or alternatively to the above ratio, a difference or other mathematical relationship may also be used to compare the patient physiological response to posture to a threshold value, where the threshold value can be established, in certain examples, using a healthy person's physiological response to posture.

Figure 2:
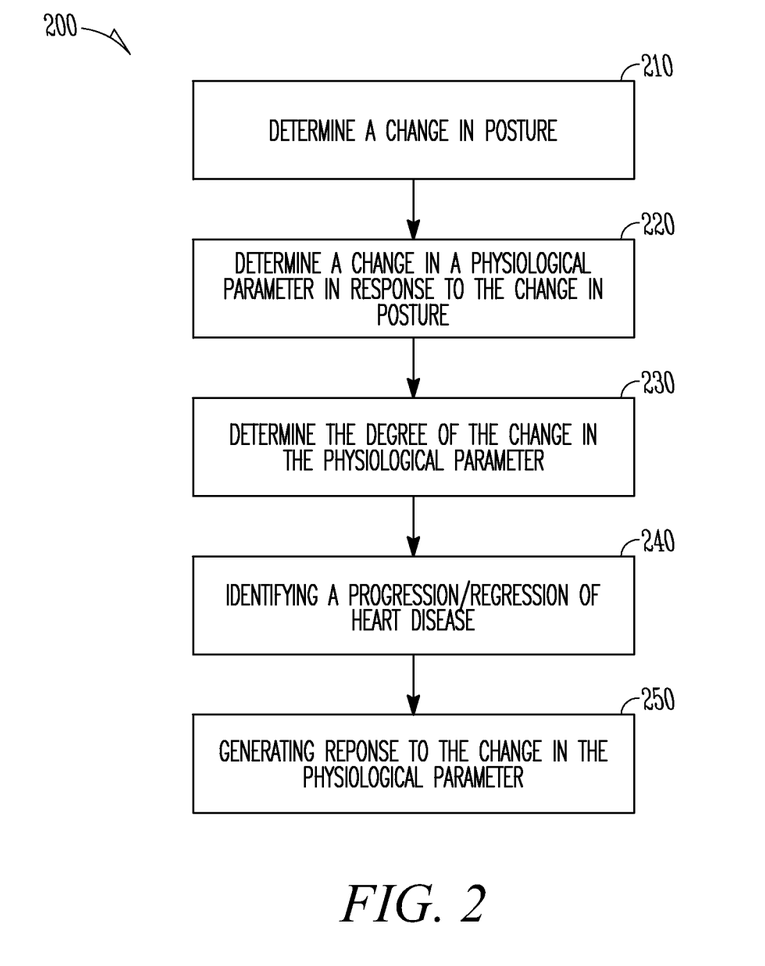
FIG. 2 illustrates an example embodiment of a process to determine a physiological response to a change in posture.

FIG. 2 is a flowchart that illustrates an example of a process 200 to determine, analyze, and respond to a postural change in a physiological parameter. At 210, a change in posture of a body is detected. At 220, a change in a physiological parameter in response to the change in posture is determined. At 230, a degree in the change of the physiological parameter is determined. This can be accomplished by comparison to a threshold value, a comparison to a trend of similar values, or the like. At 240, an identification of a heart failure status (e.g., presence, improvement, or worsening) can be identified. At 250, a therapy, alert, or other response may be generated based on the heart failure status information or directly from the postural change in the physiological parameter.

In certain examples, the device 100 includes a telemetry circuit 150, such as for communicating with an external device 160. In certain examples, the telemetry circuit 150 transmits data collected by the posture sensing circuit 140 and/or the physiological parameter sensing circuit 120, either before or after signal processing. This data may then be analyzed, such as by the external device 160 or by a health care professional to determine the patient's status. Additionally, in certain examples in which the device 100 or the external device 160 determines (e.g., using the postural change in the physiological signal) that the heart failure is worsening (such as during a decompensation episode) a resulting alert may generated and delivered to the patient or a caregiver. As illustrative examples, the alert may include one or more of an audible signal, a text message, or some other signal to draw attention to the patient's worsening condition. This may help avoid hospitalizations resulting from decompensation episodes.

Figure 3:
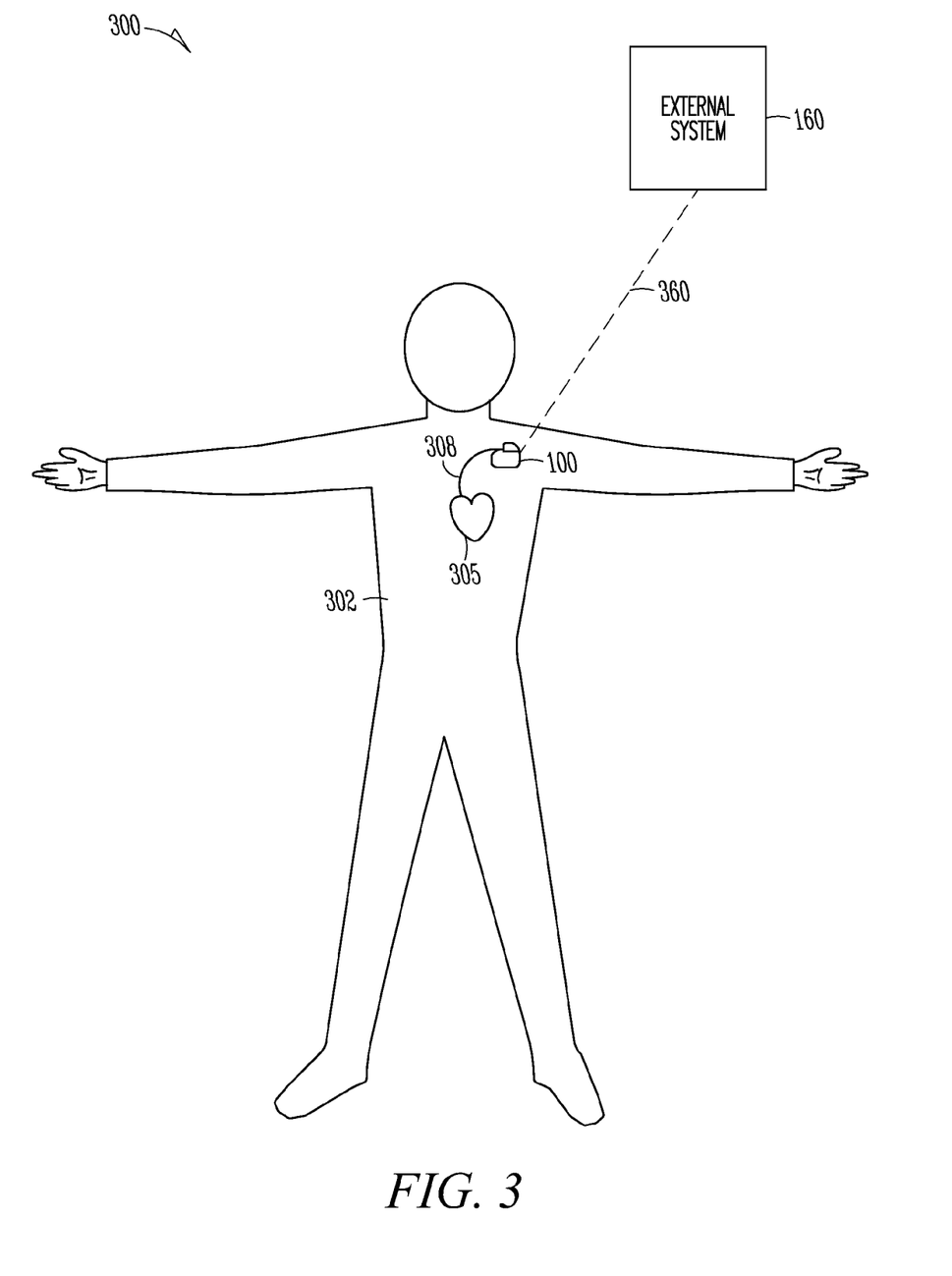
FIG. 3 illustrates an example embodiment of an implanted medical device coupled to an adjunct device.

FIG. 3 is a diagram illustrating an example of a medical device system 300 which can be used in connection with transmitting data from an implanted device 100 to an external device 160. FIG. 3 illustrates a body 302 with a heart 305. System 300 includes an implantable medical device 100, a lead system 308, an adjunct device or system 160, and a wireless telemetry link 360. Posture data, physiological parameter data, and other data may be transferred from the device 100 to the external system 160 via the telemetry link 360. The telemetered data loaded into the external system 160 can then be used for analysis and interpretation either immediately or at a later time.

In the foregoing detailed description, various features are grouped together in one or more embodiments or examples for the purpose of streamlining the disclosure. This method of disclosure is not to be interpreted as reflecting an intention that the claimed embodiments of the invention require more features than are expressly recited in each claim. Rather, as the following claims reflect, inventive subject matter lies in less than all features of a single disclosed embodiment. Thus the following claims are hereby incorporated into the detailed description of embodiments of the invention, with each claim standing on its own as a separate embodiment. It is understood that the above description is intended to be illustrative, and not restrictive. It is intended to cover all alternatives, modifications and equivalents as may be included within the scope of the invention as defined in the appended claims. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first," "second," and "third," etc., are used merely as labels, and are not intended to impose numerical requirements on their objects.

The abstract is provided to comply with 37 C.F.R. 1.72(b) to allow a reader to quickly ascertain the nature and gist of the technical disclosure. The Abstract is submitted with the understanding that it will not be used to interpret or limit the scope or meaning of the claims.

What is claimed is:

1. A method comprising:
   using an implantable medical device to determine a change in a posture of a body;
   determining a change in a physiological parameter in response to the change in posture; and
   generating a device response as a function of the change in the physiological parameter,
   wherein the physiological parameter includes one or more of a heart rate, a heart rate variability, a heart sound, a respiration rate, and a blood pressure, and the change in the physiological parameter comprises at least one of:
   a sensed change in heart rate that is less than a normal subject's change in heart rate;
   a sensed change in blood pressure that is more than a normal subject's change in blood pressure;
   a sensed change in heart sound energy that is less than a normal subject's change in heart sound energy;
   a sensed change in heart rate variability that is less than a normal subject's change in heart rate variability; and
   a sensed decrease in respiration rate; and
   further comprising comparing the change in the physiological parameter, the comparison comprising comparing (1) a ratio of the physiological parameter in the first posture to the physiological parameter in the second posture for a subject with a possible health condition, to (2) the ratio of the physiological parameter in the first posture to the physiological parameter in the second posture for a normal subject or population.

2. The method of claim 1,
   wherein the ratio comprises $100*(RPP1/RPP2-1)$,
   wherein RPP1 relates to a resting physiological parameter while in a first posture, and
   wherein RPP2 relates to a resting physiological parameter while in a second posture.

3. The method of claim 1, further comprising identifying at least one of a progression or a regression of a health condition of a subject as a function of the change in the physiological parameter.

4. The method of claim 3, including:
   trending the physiological parameter, and
   wherein identifying the health condition includes identifying one or more of a progression and a regression of heart failure status of the subject using the trending.

5. The method of claim 1, wherein generating the device response includes issuing an alert by the implantable medical device to an external device as a function of the change in the physiological parameter.

6. The method of claim 1, wherein generating the device response includes adjusting pacing therapy delivered using the implantable medical device.

7. The method of claim 1, wherein generating the device response includes adjusting neural stimulation therapy delivered using the implantable medical device.

8. The method of claim 1, wherein generating the device response includes adjusting delivery of a substance that is delivered by the implantable medical device.

9. The method of claim 8, including:
   determining whether the body has changed from a recumbent posture to a posture that is more upright than recumbent, and
   wherein adjusting delivery of a substance includes adjusting titration of a pharmaceutical in response to the determined change in posture.

10. The method of claim 1, including:
    identifying a health condition associated with congestive heart failure as a function of the change in the physiological signal, and
    wherein generating the response includes generating the response when the health condition is identified.

11. The method of claim 10, wherein identifying a health condition includes identifying an episode of congestive heart failure decompensation.

* * * * *